United States Patent [19]
Hommeltoft et al.

[11] Patent Number: 6,156,207
[45] Date of Patent: Dec. 5, 2000

[54] PROCESS FOR THE REMOVAL OF METAL COMPOUNDS FROM AN AQUEOUS ACID SOLUTION

[75] Inventors: Sven Ivar Hommeltoft, Hillerød; Susanna Lyng Røen, Hørsholm, both of Denmark

[73] Assignee: Haldor Topsoe A/S, Lyngby, Denmark

[21] Appl. No.: 09/311,791

[22] Filed: May 13, 1999

Related U.S. Application Data

[60] Provisional application No. 60/085,531, May 14, 1998.
[51] Int. Cl.[7] .................................................. B01D 15/04
[52] U.S. Cl. ........................... 210/681; 210/688; 562/124
[58] Field of Search ..................................... 210/681, 688; 562/124

[56] References Cited

U.S. PATENT DOCUMENTS

| | | | |
|---|---|---|---|
| 3,496,224 | 2/1970 | Ayers et al. ............................. | 562/124 |
| 3,882,018 | 5/1975 | Depree .................................... | 210/681 |
| 5,220,095 | 6/1993 | Hommeltoft et al. ................... | 585/720 |
| 5,245,100 | 9/1993 | Hommeltoft et al. ................... | 585/720 |
| 5,603,812 | 2/1997 | Hommeltoft .............................. | 203/29 |

*Primary Examiner*—Ivars Cintins
*Attorney, Agent, or Firm*—Ostrolenk, Faber, Gerb & Soffen, LLP

[57] ABSTRACT

Process for the selective removal of metallic ion and/or ion ammonium impurities from water soluble acid compound comprising the steps of preparing an aqueous solution of the acid compound containing the impurities;

contacting the aqueous solution with a cation exchange resin and removing selectively the metal-ion and/or ammonium ion impurities from the solution at condition being effective in the exchange of cations; and withdrawing an aqueous solution of the acid compound being substantially free of the impurities.

1 Claim, No Drawings

PROCESS FOR THE REMOVAL OF METAL COMPOUNDS FROM AN AQUEOUS ACID SOLUTION

This application claims the benefit of U.S. Provisional Application Ser. No. 60/085,531, filed May 14, 1998.

The present invention relates parfication of water soluble acids and acid compounds. In particular, by the invention metallic impurities are selectively removed from aqueous solution containing acid compounds and metals being in the form of metal salts formed with the acids.

Those metals salts, e.g. iron and nickel salts may form due to corrosion of metallic construction materials employed in chemical processes with the acids. In a large number of industrial processes acids are used as catalysts which are desirable to recover and reuse in a number of process cycles. Thus, recently use of perfluorinated acids in the alkylation of hydrocarbon has been described in U.S. Pat. Nos. 5,220,095 and 5,245,100.

Perfluorinate sulphonic acid catalysts employed in the above processes are preferably in anhydrous form in order to be effective alkylation catalysts U.S. Pat. No. 5,603,812 discloses a process to recover the perfluorinated sulphonic acids from aqueous solution by addition of alkyl ammonium salts from which the acids can be recovered in substantially anhydrous form.

Though the known processes provide a useful tool in the recovery of valuable acid catalysts, the recovered acid may still contain undesired corrosion products such as iron or nickel salts of the acids or ammonium salts formed by corrosion of metallic material used in the process equipment or nitrogen-containing impurities in process feed.

It is, thus, an object of the invention to remove selectively metallic compounds and/or ammonium salts from an aqueous solution containing an acid and/or alkyl ammonium salts of the acid.

The above object is realized by this invention providing a process for the selective removal of metallic ion and/or ammonium ion impurities from a water soluble acid compound comprising the steps of preparing an aqueous solution of the acid compound containing the impurities;

contacting the aqueous solution with a cation exchange resin and removing selectively the metal ion and/or ammonium ion impurities from the solution at condition being effective in the ion exchange of cations; and withdrawing an aqueous solution of the acid compound being substantially free of the impurities.

For use in the inventive process, suitable cation exchange resins will be selected from the group of sulphonic acid or phosphoric acid group containing cation exchange materials, preferably in form of resins as commercially available. These ion exchange materials have high affinity to metal cations and ammonium ions, even if the exchange resin is already exchanged with alkyl ammonium ions, which are then exchanged with the metal and ammonium ions.

The above process is in particular useful in the purification of spent perfluoro alkyl sulphonic acid alkylation catalyst, which typically is in a first step recovered by aqueous extraction with addition of an alkyl amine to allow final recovery of the acid in its anhydrous form as described in the aforementioned U.S. Pat. No. 5,603,812. By the inventive process, it is then possible to further remove metal and ammonium ion impurities from the aqueous extract with the acid alkyl amine and the acid without loss of alkyl ammonium ions.

EXAMPLE 30 g sulphonic acid ion exchange resin of the type Amberlyst 15 were wetted with demineralized water and loaded into a 0.26 m (volume 80 ml) column.

An aqueous solution containing 0.45 wt % Fe-triflate $(Fe(OTf)_2)$, 0.37 wt % Ni-triflate $(Ni(OTf)_2)$ 2.26 wt % triethylammoniumtriflate $(Et_3NHOTf)$, 1.53 wt % ammoniumtriflate $(NH_4OTf)$ and 2.22 wt % trifluoromethanesulphonic acid (TfOH) was passed through the packed column at a flow rate of 2.15 ml/min. and a temperature of 25%. Samples of the effluent were collected at different runtimes. The content of Ni, Fe, $NH_4^+$ and $Et_3NH^+$ ions was then determined by ion chromatography in each sample. The results obtained in this example and conditions used are summarized in the Table below.

TABLE

| Sample No. | Run-time min. | Sample weight/g | Content of Ni/ppm | Fe/ppm | $NH4^{+/-}$ ppm | TEAH+/% |
|---|---|---|---|---|---|---|
| 1 | 48 | 89.2 | 0.2 | 0.7 | 0.8 | 0.00002 |
| 2 | 188 | 94.4 | 0.1 | 0.6 | 0.4 | 0.00005 |
| 3 | 288 | 112.1 | 0.1 | 0.7 | 125 | 1.39 |
| 4 | 337 | 105.4 | 0.1 | 1.0 | 1080 | 1.23 |
| 5 | 381 | 89.42 | 0.1 | 0.4 | 1560 | 1.23 |
| 6 | 581 | 98.98 | 4.6 | 3.0 | 1650 | 1.07 |
| 7 | 619 | 73.05 | 18.0 | 10.0 | 1640 | 096 |
| 8 | 670 | 109.37 | 150 | 93.0 | 1505 | 0.93 |
| 9 | 725 | 118.21 | 530 | 335 | 1430 | 0.91 |

$TfO^-$ concentration is constant during sampling. It is apparent from the above results that undesired Ni, Fe and ammonium ions are more strongly bound on the cation exchange material than TEAH ions, which allows selective removal of the above ions from the solution.

What is claimed is:

1. Process for the selective removal of metallic ion and ammonium ion impurities from a perfluoro alkyl sulphonic acid, comprising the steps of:

preparing an aqueous solution of said acid containing the impurities;

contacting the aqueous solution with a cation exchange resin and removing selectively the metallic ion and ammonium ion impurities from the solution at conditions effective in the exchange of cations; and withdrawing an aqueous solution of the perfluoro alkyl sulphonic acid compound being substantially free of the impurities.

* * * * *